(12) United States Patent
Rosensweet et al.

(10) Patent No.: US 10,660,905 B2
(45) Date of Patent: May 26, 2020

(54) COMPOSITION AND METHOD TO AID IN HORMONE REPLACEMENT THERAPY

(71) Applicants: Daved Rosensweet, Sarasote, FL (US); Joshua B. Rosensweet, Sarasota, FL (US)

(72) Inventors: Daved Rosensweet, Sarasote, FL (US); Joshua B. Rosensweet, Sarasota, FL (US)

(73) Assignee: THE MENOPAUSE METHOD, INC., Longboat Key, FL (US)

( * ) Notice: Subject to any disclaimer, the term of this patent is extended or adjusted under 35 U.S.C. 154(b) by 0 days.

(21) Appl. No.: 16/355,935

(22) Filed: Mar. 18, 2019

(65) Prior Publication Data
US 2019/0307774 A1    Oct. 10, 2019

Related U.S. Application Data

(62) Division of application No. 15/944,842, filed on Apr. 4, 2018, now Pat. No. 10,285,998.

(51) Int. Cl.
| | | |
|---|---|---|
| A61K 31/57 | (2006.01) | |
| A61K 31/568 | (2006.01) | |
| A61K 31/565 | (2006.01) | |
| A61K 47/46 | (2006.01) | |
| A61K 9/10 | (2006.01) | |
| A61K 9/107 | (2006.01) | |
| A61K 47/44 | (2017.01) | |

(52) U.S. Cl.
CPC ............... *A61K 31/57* (2013.01); *A61K 9/10* (2013.01); *A61K 9/107* (2013.01); *A61K 31/565* (2013.01); *A61K 31/568* (2013.01); *A61K 47/44* (2013.01); *A61K 47/46* (2013.01)

(58) Field of Classification Search
CPC ........................................................ A61K 31/57
See application file for complete search history.

(56) References Cited

U.S. PATENT DOCUMENTS

| | | | | |
|---|---|---|---|---|
| 5,527,788 A | * | 6/1996 | Svec | A61K 31/565 |
| | | | | 514/169 |
| 6,623,761 B2 | * | 9/2003 | Hassan | A61K 9/14 |
| | | | | 424/489 |
| 2005/0058731 A1 | * | 3/2005 | Beaurline | A61K 8/347 |
| | | | | 424/736 |

FOREIGN PATENT DOCUMENTS

WO    WO 2012/120290    * 9/2012

* cited by examiner

*Primary Examiner* — Rei Tsang Shiao
(74) *Attorney, Agent, or Firm* — James D. Parker

(57) ABSTRACT

A pharmaceutical two-phase admixture for topical application, transdermal or transmucosal, characterized by components in two phases, a liquid and a solid, adapted for topical application, transdermal or transmucosal, to various skin and/or mucosal surface areas of the body is disclosed. The solid phase is comprised of one or more bio-identical hormones and the liquid phase is comprised of one or more excipient carrier oils. The bio-identical hormone component is comprised of one or more of Bi-Est, testosterone, progesterone, and dehydroepiandrosterone. The excipient carrier oil component is comprised of one or more of jojoba oil, evening primrose oil, and borage seed oil. The pharmaceutical admixture is especially useful in a regime of hormone replacement therapy.

9 Claims, 2 Drawing Sheets

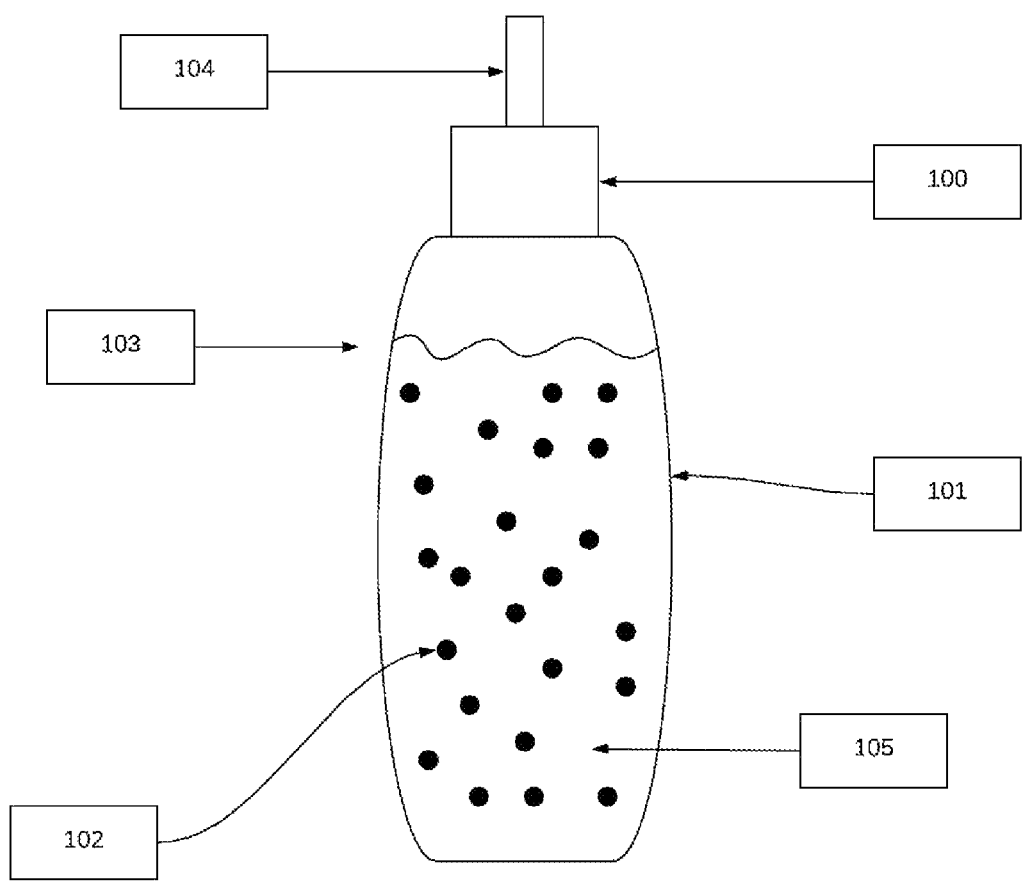

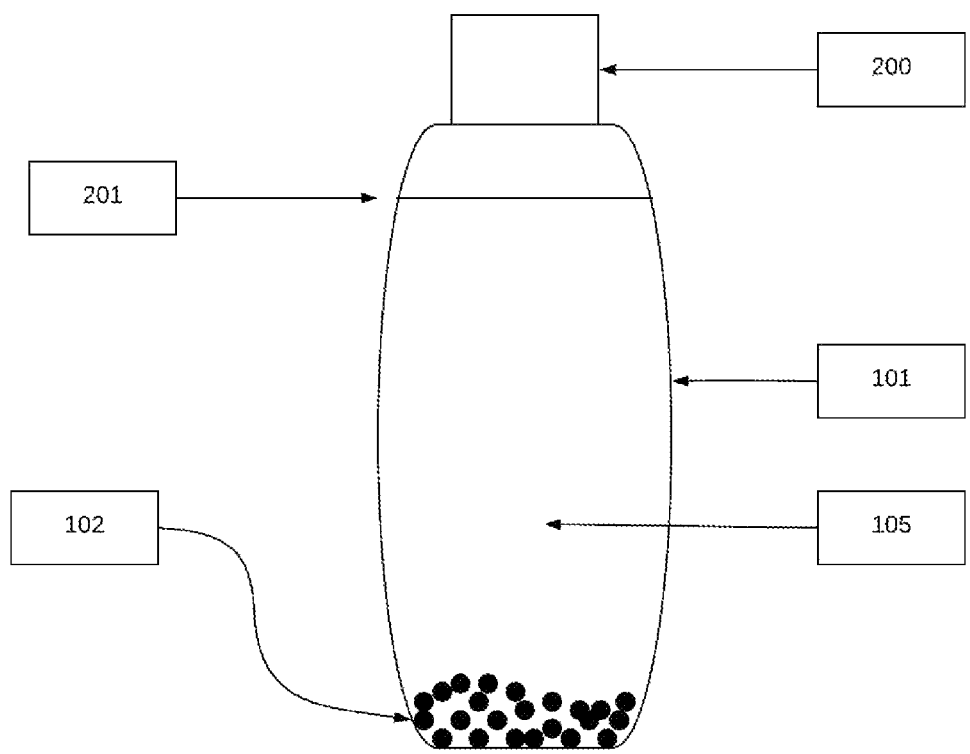

COMPOSITION AND METHOD TO AID IN HORMONE REPLACEMENT THERAPY

CROSS-REFERENCE TO RELATED APPLICATIONS

This patent application is a Divisional of the U.S. Non-Provisional application Ser. No. 15/944,842, filed Apr. 4, 2018 (now pending), the disclosure of which is incorporated by reference in its entirety.

FIELD OF THE INVENTION

This disclosure of two-phase admixtures and methodology relates to hormone replacement therapy.

BACKGROUND OF THE INVENTION

As noted in U.S. Pat. No. 6,228,852 B1,
"Progesterone is a steroid hormone that is produced by the ovaries during a woman's child-bearing years. Progesterone is also made, although in smaller amounts, by the adrenal glands in both sexes and by the testes in males. An astonishing variety of physiological functions are mediated by progesterone (See e.g., Lee, 1993, Natural Progesterone, BLL Publishing, Sebastopol, Calif.). For example, progesterone, which surges following ovulation, maintains the secretory endometrium and thus, helps to ensure the survival of the embryo and fetus. It also acts as a diuretic, an antidepressant, and as a precursor of corticosteroids and of other sex hormones, notably estrogen and testosterone. There is also evidence that progesterone affords protection against loss of libido, osteoporosis, endometrial cancer, breast cancer, and fibrotic cysts."

As women age, they experience a decline in the production of progesterone, estrogens and androgens. In addition to uncomfortable symptoms, such as hot flashes, sleep disturbance, and cognitive challenges, which are frequently experienced at around the time of menopause, there is an increase in the prevalence of debilitating conditions, including heart disease, loss of skeletal muscle, osteoporosis, cognitive decline and the possibility of stroke.

At present, a common form of treatment for many of the above conditions is oral administration of estrogen. In addition to oral administration, estrogen may be introduced to the body by a vaginal suppository, intramuscular injection, buccal mucosa pouch and in sublingual troches, transdermal patch, creams and gels, nasal mucosal spray, and subcutaneous implant. In a similar manner to estrogen, other hormones such as progesterone, testosterone, and dehydroepiandrosterone (DHEA) may be administered as active pharmacological ingredients in support of a hormone replacement therapy regime. However, there is the possibility of substantial adverse systemic side effects arising from the misuse of any of these replacement hormones. These adverse effects include possible contributions to endometrial hyperplasia, endometrial carcinoma, breast cancer, thrombophlebitis, pulmonary embolism, cerebral thrombosis, mental depression, nausea, insomnia, fluid retention, migraine headache, liver dysfunction, weight gain, acne and more.

In addition to systemic side effects, there are specific local side effects associated with the method of administration. U.S. Pat. No. 8,026,228 teaches oral administration of hormones, but due to gastrointestinal degradation of the drug and the "first pass effect" in the liver, oral administration of estrogens requires higher than medically necessary doses to obtain the proper therapeutic level in the body thus possibly elevating the probability of systematic side effects. U.S. Pat. No. 8,629,129 teaches the use of vaginal suppositories which can, if the woman is having intercourse, be transmitted to her partner. Suppositories can also cause irritation due to a high local drug concentration, and can have a tendency to dislodge and exit the vagina during activity. U.S. Publication. No. 2005/0282749 teaches administration via intramuscular injection, but such administration may require a visit to a medical facility, is inconvenient for frequent doses, and can cause site injection irritation due to a high local drug concentration. This method, as well as pellet injection, does not allow for minor dosage alterations based upon symptoms of insufficiency or excess varying with actual day to day needs. U.S. Pat. No. 7,951,398 teaches transdermal patches, which while popular, require the diffusion of drugs across a limited surface area that can cause irritation due to a high drug concentration, and furthermore, penetration enhancers, often used in transdermal patches, can also cause skin irritation. U.S. Pat. No. 6,117,446 teaches buccal administration to the mucosal membranes of the mouth, but such administration can lead to significant quantities of the hormones being swallowed, thus subject to the "first pass effect." It can also lead to high drug concentration irritation like other methods. PCT Publication No. WO1998006404 teaches using a subcutaneous implant, but such administration requires a visit to a medical facility and does not lend itself well to monthly breaks or mini-variations in hormonal dosage needs as is common. Also, it is inconvenient for frequent doses, and furthermore, the implant site is subject to irritation due to a localized concentration of the drug. Additionally, if required, the removal of the implant may prove to be difficult. U.S. Publication No. 2006/0147385 teaches the use of nasal mucosal spray, but such application requires a high drug concentration due to the short application time, has a rapid absorption time thus producing excessive hormonal dosage peaks, and is likewise subject to induce local irritation. U.S. Publication No. 2004/0266688 teaches intravenous administration, but such administration requires excessively frequent visits to a medical facility, as well as also producing unphysiological hormonal dosage peaks, and is inconvenient for frequent doses.

SUMMARY OF THE INVENTION

An object of the two-phase admixtures and methodology disclosed herein is to solve or at least significantly improve upon the deficiencies of the prior art noted above.

One aspect of the two-phase admixtures and methodology disclosed herein there is provided a two-phase admixture comprised of two phases, a liquid and a solid, where the liquid phase is primarily comprised of one or more excipient carrier oils and the solid phase is comprised of one or more bio-identical hormone formulations useful in hormone replacement therapy.

Another aspect of the two-phase admixtures and methodology disclosed herein there is provided a method of preparing the two-phase bio-identical hormone admixture above for use by a female patient. This method is appropriately practiced by licensed compounding pharmacists.

Still, another aspect of the two-phase admixtures and methodology disclosed herein there is provided a method of self-application of the above two-phase bio-identical hormone admixture to the appropriate parts of the female patient's skin and mucous membranes.

Further objects, features, and advantages of the present application will be apparent to those skilled in the art from detailed consideration of the embodiments that follow.

BRIEF DESCRIPTION OF THE DRAWINGS

FIG. 1 is a schematic front view of the dispensing bottle body 101 showing the temporarily dispersed solid bio-identical hormone 102 in excipient carrier oil 105. The said dispensing bottle body 101 is capped by a dispensing cap 100 which contains an orifice reducer 104. Said orifice reducer 104 has an inside diameter appropriate to dispense drops of a specific volumetric quantity of the two-phase bio-identical hormone admixture. The surface of the two-phase bio-identical hormone admixture in the dispensing bottle 101 is indicated by the wavy surface line 103. Surrounding the temporarily dispersed solid bio-identical hormone 102 is the excipient carrier oil 105 comprised of one or more oils. This is the expected state of the two-phase bio-identical hormone admixture just after agitation and just prior to self-application by the female patient where the solid bio-identical hormone 102 has been temporarily dispersed in the excipient carrier oil 105.

FIG. 2 is a schematic front view of the dispensing bottle body 101 showing the settled solid bio-identical hormone 102 at the bottom of the dispensing bottle body 101. The excipient carrier oil 105 for the most part remains above the solid bio-identical hormone 102. The said dispensing bottle body 101 is sealed by a sealing cap 200 which fits over the dispensing cap 100 and the orifice reducer 104. The surface of the two-phase bio-identical hormone admixture in the dispensing bottle 101 is indicated by the horizontal straight line surface line 201. This is the expected state of two-phase bio-identical hormone admixture in storage and prior to the application of agitation to temporarily suspend the solid bio-identical hormone 102 in the liquid excipient carrier oil 105 comprised of one or more oils.

DETAILED DESCRIPTION OF THE PREFERRED EMBODIMENT

While the present two-phase admixtures and methodology are disclosed with respect to the preferred embodiments described below and in the figures, the present two-phase admixtures and methodology are limited only by the metes and bounds of the claims that follow.

The two-phase admixtures and methodology disclosed herein offer a significantly improved approach to hormone replacement therapy. This approach offers increased safety, minimizing the possibility of adverse side effects because of the two phase delivery system, suspending the bio-identical hormones in oil(s), and thus eliminating the need to use toxic solvents to bring hormones into solution. This approach also offers greater flexibility in terms of delivering, via drops, the amounts of individual bio-identical hormones as well as minimizing the likelihood of localized, application site specific adverse side effects.

For a general understanding of the disclosed two-phase admixtures and methodology, reference is made to the drawings. In the drawings, like reference numerals have been used to designate identical elements. In describing the disclosed two-phase admixtures and methodology, the following terms have been used in the description.

The term "bio-identical hormone" refers to hormones that are chemically and structurally identical to those humans naturally produce and are derived from plant sources by Pharmaceutical manufacturers.

The term "Bi-Est" refers to a combination of estradiol and estriol in a specific proportion. A preferred proportion has an upper range of 80 percent by weight estradiol to 20 percent by weight estriol and a lower range of 20 percent by weight estradiol to 80 percent by weight estriol.

The term "jojoba oil" refers to the extract of the seeds of the *Simmondsia chinensis* plant commonly found growing in the desert southwest.

The term "evening primrose oil" refers to the extract from the plant *Oenothera biennis* which is one of many species of the genus *Oenothera* found in North America.

The term "borage seed oil" refers to the extract from the seeds of the *Borago officinalis* plant.

The term "mg" refers to the standard abbreviation for milligram, a metric unit of weight.

The term "mL" refers to the standard abbreviation for milliliter, a metric unit of volume.

The term "admixture" or "combination" refer to a material composed of one or more separate ingredients or components.

The term "liquid phase" or "excipient carrier oil" or "liquid excipient carrier oil" refers to a miscible liquid solution comprising one or more of jojoba oil, evening primrose oil, and borage seed oil.

The term "solid phase" or "solid bio-identical hormone" or "solid bio-identical hormone formulation" refers to a solid comprising one or more of Bi-Est, progesterone, testosterone, and dehydroepiandrosterone.

The term "two-phase admixture" or "two-phase admixtures" or "two-phase bio-identical hormone admixture" refers to a combination of one or more of the liquid phase components combined with one or more of the solid phase components in a specifically prescribed combination.

The term "appropriate laboratory container" refers to laboratory glassware designed to aid in the quantitative measurement of liquid volumes such as volumetric flasks.

The term "appropriate application container" refers to the dispensing bottle body 102 combined with the orifice reducer 104 and dispensing cap 100 and, while in storage, the sealing cap 200.

The term "first pass effect" refers to the mechanism of hormone metabolism that occurs with oral administration of a hormone. This mechanism is as follows: the hormone is absorbed from the intestinal tract and then travels directly to the liver. In the liver a substantial percentage of the administered hormone is immediately metabolized thus becoming ineffective for having any hormonal effect in the body. Another portion of that administered hormone is not metabolized, and does then pass into general circulation to have hormonal effects as it circulates throughout the body.

Unlike all other formulations used for hormone replacement therapy, the two-phase bio-identical hormone admixture disclosed herein is composed of two distinct phases, a solid and a liquid. It is common for other formulations to be composed of a solid, a semi-solid, a gel, a cream or a liquid. To achieve these single phase formulations additional components are introduced to promote the final single phase form. For example, ovarian and adrenal steroid hormones are sparingly soluble in lipophilic media; hence, it is necessary to introduce various strong solvents into the mixture to accomplish hormone solubility. These strong solvents have toxic potential, as evidenced in the scientific medical literature (for example, Kevin C. Wilson, MD; Christine Reardon, MD; Arthur C. Theodore, MD; and Harrison W. Farber, MD, FCCP; "Propylene Glycol Toxicity: A Severe Iatrogenic Illness in ICU Patients Receiving IV Benzodiazepines"; CHEST Journal, September 2005, Volume 128, No.

3, pages 1674-1681). Another beneficial aspect of the two-phase bio-identical hormone admixtures and methodology disclosed herein is to eliminate such localized application site irritation.

The most appropriate way to define the composition of the two-phase bio-identical hormone admixture is in terms of the distinct phases. The liquid phase is comprised of one or more of jojoba oil, evening primrose oil, and borage seed oil. This particular combination of oils was discovered via extensive experimentation and is necessary to achieve the final mixture viscosity that is essential to providing drops of a specific volume of the two-phase admixture using the orifice reducer 104. For one exemplary preferred liquid phase containing all of the above three oils, the major component is jojoba oil in which the composition can range from 90.0 volume percent (90.0 vol %) to 96.0 volume percent (96.0 vol %), the evening primrose oil composition can range from 2.5 volume percent (2.5 vol %) to 6.5 volume percent (6.5 vol %), and the borage seed oil composition can range from 1.5 volume percent (1.5 vol %) to 3.5 volume percent (3.5 vol %). An exemplary preferred method of preparation of a specific excipient carrier oil mixture having all three of the above excipient carrier oil components of specified amounts would include the following steps:

(1) Measure out 6.3 mL of evening primrose oil.
(2) Measure out 3.4 mL of borage seed oil
(3) Combine the above amounts of evening primrose oil and borage seed oil in a appropriate laboratory container (like a 100 mL volumetric flask)
(4) Add jojoba oil up to slightly less than the 100 mL flask mark.
(5) Agitate well to insure complete mixing.
(6) Add further jojoba oil up to the 100 mL flask mark.
(7) Agitate further to insure complete miscibility. The evening primrose oil concentration is 6.3 volume percent, the borage seed oil concentration is 3.4 volume percent, and the jojoba oil component is 90.3 volume percent.

The solid phase is comprised of one or more bio-identical hormones of Bi-Est, progesterone, testosterone, and dehydroepiandrosterone. The composition of Bi-Est is composed of estradiol and estriol combined in a ratio that has a preferred upper range from between 20 weight percent (20 wt %) estradiol to 80 weight percent estriol (80 wt %) and a preferred lower range of 80 weight percent (80 wt %) estradiol to 20 weight percent (20 wt %) estriol. Of this combined mixture of estradiol and estriol, the concentration in the final two-phase bio-identical hormone admixture (combined solid and liquid phases) ranges between 5 mg per mL and 80 mg per mL. The other solid bio-identical hormones are prepared with preferred concentrations in the final two-phase bio-identical hormone admixture as follows:

| | |
|---|---|
| Progesterone | 10 mg/mL to 200 mg/mL |
| DHEA | 10 mg/mL to 200 mg/mL |
| Testosterone | 10 mg/mL to 200 mg/mL. |

An exemplary preferred method for compounding the two-phase bio-identical hormone admixture starts with the preparation of the liquid phase as indicated above. Depending upon the prescription for the two-phase bio-identical hormone admixture the liquid phase could have one or more excipient carrier oil components. As an example, if the final volume of two-phase bio-identical hormone admixture is to be 100 mL, then the appropriate amount of a solid phase bio-identical hormone would be added to an appropriate vessel, like a 100 mL volumetric flask, and the liquid phase, just prepared, would be added to bring the total volume up to 100 mL. Hence, as a further example, if the concentration of a solid phase bio-identical hormone is prescribed to be 50 mg per mL, then 5.0 grams (or equivalently 5000 mg) of the hormone would be added to the 100 mL volumetric flask and the liquid phase would be added to bring the total volume to 100 mL.

The self-application of the two-phase bio-identical hormone admixture of excipient carrier oil and solid bio-identical hormone is made straight-forward by the incorporation of an orifice reducer 104 which may have one of several different diameters. The determination of a diameter which will dispense a drop having a known and constant volume depends upon several factors. A major factor is the fluid viscosity. Pure component fluids like jojoba oil, evening primrose oil, or borage seed oil are Newtonian fluids where their viscosity is only a function of temperature. Also a mixture of jojoba oil, evening primrose oil, and borage seed oil (the components of the excipient carrier oil) is a Newtonian fluid. The viscosity of the excipient carrier oil will depend on the volumetric concentration of the components and can be considered to be constant for a specific mixture. Also being a Newtonian fluid, the viscosity of the excipient carrier oil does not change in response to agitation. It should be noted that combining jojoba oil, evening primrose oil, and borage seed oil (the excipient carrier oil) results in a fluid having a viscosity somewhat less than that of jojoba oil, but greater than either evening primrose oil or borage seed oil. Hence, by changing the relative concentrations of the components that make up the excipient carrier oil, the viscosity of the mixture can be adjusted to a value where liquid flow and mixing properties are favorable. However, the addition of a solid bio-identical hormone to the excipient carrier oil turns the resulting two-phase bio-identical hormone admixture into a non-Newtonian fluid where the agitation history influences the viscosity of the two-phase bio-identical hormone admixture. Hence, to obtain droplets of consistent volume and constant solid phase content from the orifice reducer 104 the temperature of the two-phase admixture, the composition of the two-phase admixture, and the agitation history of the two-phase admixture must remain uniform. Considerable experimentation has allowed a determination as to the appropriate diameter of the orifice reducer 104 to get a dispensed drop of a specific volume having specific solid phase content for a specific two-phase bio-identical hormone admixture and agitation history.

An exemplary preferred method of self-application of the two-phase bio-identical hormone admixture is as follows. After the physician prescribes the two-phase bio-identical hormone admixture, the two-phase bio-identical hormone admixture is prepared by the compounding pharmacist; subsequently, the pharmacist installs the prescribed orifice reducer 104 diameter, installs the dispensing cap 100, and then installs the sealing cap 200 which fits over the previously installed two orifice reducer 104 and the dispensing cap 100. The patient agitates the dispensing bottle 101 according to instructions, removes the sealing cap 200, and allows the prescribed number of drops of two-phase bio-identical hormone admixture to be applied to one forearm. Two forearms are then rubbed together allowing the two-phase bio-identical hormone admixture to be absorbed into the skin over a short period of time. This is repeated at prescribed time intervals. Alternatively, a second exemplary preferred method of self-application would be to dispense the two-phase bio-identical hormone admixture to one of the inner thighs rubbing the two-phase bio-identical hormone admixture into the skin. Other obvious areas of application are the abdomen, outer thighs, outer shoulders and mucous membranes.

These methods of application are advantaged in that:
(1) The greater surface area of application of the two-phase bio-identical hormone admixture, which is very large compared to transdermal patches, reduces irritation due to reduced localized active pharmaceutical hormone concentration,
(2) The actual application site can be varied even further reducing the possibility of application site irritation,
(3) Rubbing to administer the two-phase bio-identical hormone admixture generates shear force, pressure, and heat by friction which aids in the adsorption of the two-phase formulation into the skin, and
(4) Does not require penetration enhancers to promote diffusion into the skin.

Other advantages of the two-phase bio-identical hormone admixture and these methods of application include:
(1) Does not require solvents to dissolve the active pharmaceutical solid phase hormones thus eliminating any toxic exposure from the solvents,
(2) Does not require a visit to a medical facility,
(3) Convenient for frequent doses,
(4) Just the appropriate dosage of the two-phase bio-identical hormone admixture can be administered to obtain the appropriate therapeutic concentration of replacement hormones in the body thereby reducing the possibility of adverse side effects.

Of further note, clinical trials are in progress and ongoing for the two-phase admixtures disclosed herein.

It will be apparent to those skilled in the art that various modifications and variations can be made to the two-phase admixtures and methodology disclosed herein. Thus, it is intended that the present two-phase admixtures and methodology cover such modifications and variations, provided they come within the scope of the appended claims and their equivalents.

The disclosure of all publications cited above is expressly incorporated herein by reference in their entireties to the same extent as if each were incorporated by reference individually.

What is claimed is:

1. A pharmaceutical two-phase bio-identical hormone admixture comprising a solid bio-identical hormone formulation of testosterone wherein the overall concentration of testosterone in said admixture is between 10 mg per mL and 200 mg per mL and an excipient carrier oil wherein said excipient carrier oil is comprised of one or more of jojoba oil, evening primrose oil, and borage seed oil.

2. The pharmaceutical two-phase bio-identical hormone admixture of claim 1, wherein said excipient carrier oil is jojoba oil.

3. The pharmaceutical two-phase bio-identical hormone admixture of claim 1, wherein said excipient carrier oil is comprised of jojoba oil wherein the concentration of jojoba oil is between 90.0 volume percent and 96.0 volume percent, evening primrose oil wherein the concentration of evening primrose oil is between 2.5 volume percent and 6.5 volume percent, and borage seed oil wherein the concentration of borage seed oil is between 1.5 volume percent and 3.5 volume percent.

4. A pharmaceutical two-phase bio-identical hormone admixture comprising a solid bio-identical hormone formulation of progesterone wherein the overall concentration of progesterone in said admixture is between 10 mg per mL and 200 mg per mL and an excipient carrier oil wherein said excipient carrier oil is comprised of one or more of jojoba oil, evening primrose oil, and borage seed oil.

5. The pharmaceutical two-phase bio-identical hormone admixture of claim 4, wherein said excipient carrier oil is jojoba oil.

6. The pharmaceutical two-phase bio-identical hormone admixture of claim 4, wherein said excipient carrier oil is comprised of jojoba oil wherein the concentration of jojoba oil is between 90.0 volume percent and 96.0 volume percent, evening primrose oil wherein the concentration of evening primrose oil is between 2.5 volume percent and 6.5 volume percent, and borage seed oil wherein the concentration of borage seed oil is between 1.5 volume percent and 3.5 volume percent.

7. A pharmaceutical two-phase bio-identical hormone admixture comprising a solid bio-identical hormone formulation of dehydroepiandrosterone (DHEA) wherein the overall concentration of dehydroepiandrosterone (DHEA) in said admixture is between 10 mg per mL and 200 mg per mL and an excipient carrier oil wherein said excipient carrier oil is comprised of one or more of jojoba oil, evening primrose oil, and borage seed oil.

8. The pharmaceutical two-phase bio-identical hormone admixture of claim 7, wherein said excipient carrier oil is jojoba oil.

9. The pharmaceutical two-phase bio-identical hormone admixture of claim 7, wherein said excipient carrier oil is comprised of jojoba oil wherein the concentration of jojoba oil is between 90.0 volume percent and 96.0 volume percent, evening primrose oil wherein the concentration of evening primrose oil is between 2.5 volume percent and 6.5 volume percent, and borage seed oil wherein the concentration of borage seed oil is between 1.5 volume percent and 3.5 volume percent.

* * * * *